United States Patent
Dumpson et al.

(10) Patent No.: US 8,784,351 B2
(45) Date of Patent: Jul. 22, 2014

(54) COMPRESSION GARMENT

(75) Inventors: Carmella Dumpson, Port Melbourne (AU); Sinead O'Donovan, Port Melbourne (AU)

(73) Assignee: Gilheany & O'Donovan Holdings Pty, Port Melbourne VIC (AU)

( * ) Notice: Subject to any disclaimer, the term of this patent is extended or adjusted under 35 U.S.C. 154(b) by 765 days.

(21) Appl. No.: 12/405,331

(22) Filed: Mar. 17, 2009

(65) Prior Publication Data

US 2009/0254017 A1    Oct. 8, 2009

Related U.S. Application Data

(60) Provisional application No. 61/043,485, filed on Apr. 9, 2008.

(30) Foreign Application Priority Data

Mar. 17, 2008    (AU) ................................ 2008901285

(51) Int. Cl.
*A61F 13/00* (2006.01)
*A41B 9/08* (2006.01)

(52) U.S. Cl.
USPC ........... 602/67; 602/61; 2/401; 2/406; 2/78.3; 450/100; 450/104; 450/155

(58) Field of Classification Search
USPC .................. 602/60–61, 67; 2/236, 400–401, 2/403–407, 409, 466, 78.3; 450/155, 450/100–101, 104, 123
See application file for complete search history.

(56) References Cited

U.S. PATENT DOCUMENTS

| | | | |
|---|---|---|---|
| 2,641,258 A * | 6/1953 | Rutledge | 602/67 |
| 4,343,044 A | 8/1982 | Borda et al. | |
| 4,538,615 A | 9/1985 | Pundyk | |
| 4,625,336 A | 12/1986 | Derderian | |
| 5,784,723 A * | 7/1998 | Noble et al. | 2/400 |
| 6,041,441 A | 3/2000 | Counts et al. | |
| 6,062,946 A | 5/2000 | Rosenberg | |
| 6,159,070 A * | 12/2000 | Schwartz et al. | 450/155 |
| 6,247,185 B1 * | 6/2001 | Gardon-Mollard | 2/409 |
| 6,283,124 B1 | 9/2001 | Schleuning et al. | |
| 6,430,752 B1 | 8/2002 | Bay | |
| 6,446,264 B2 | 9/2002 | Fairhurst et al. | |
| 6,755,052 B1 * | 6/2004 | Sytz | 66/196 |
| 6,918,140 B1 * | 7/2005 | Cooper | 2/228 |
| 7,814,575 B2 * | 10/2010 | Hendrickson et al. | 2/227 |

(Continued)

FOREIGN PATENT DOCUMENTS

WO    WO 2007/112494    10/2007

OTHER PUBLICATIONS

"What is 'Jersey Stitch'—Definition and Explanation", TextileGlossary.com, accessed Sep. 29, 2011 from http://textileglossary.com/terms/jersey-stitch.html.*

*Primary Examiner* — Patricia Bianco
*Assistant Examiner* — Kari Petrik
(74) *Attorney, Agent, or Firm* — Marvin Petry; Stites & harbison PLLC

(57) ABSTRACT

A compression garment has panels of elasticized fabric joined by seams of flat lock stitching to define, when worn, specific areas of compression, areas of compression being the perineum, caesarian wound area and rectus abdominus muscles or the perineum and the pelvic joints.

20 Claims, 5 Drawing Sheets

(56) References Cited

U.S. PATENT DOCUMENTS

| | | | |
|---|---|---|---|
| 8,092,273 B2* | 1/2012 | Shinomiya | 450/97 |
| 2005/0229293 A1* | 10/2005 | Miller | 2/403 |
| 2007/0220660 A1* | 9/2007 | Roesch et al. | 2/403 |
| 2009/0025115 A1 | 1/2009 | Duffy et al. | |
| 2009/0113596 A1* | 5/2009 | Young | 2/69 |
| 2012/0309265 A1* | 12/2012 | Abrams | 450/95 |

* cited by examiner

COMPRESSION GARMENT

CROSS REFERENCE TO RELATED APPLICATIONS

This application claims benefit of U.S. Provisional Application No. 61/043,485 filed Apr. 9, 2008 (which is hereby incorporated by reference).

INTRODUCTION

This invention relates to a compression garment and more particularly a compression garment for use in ante and post natal recovery.

BACKGROUND OF THE INVENTION

Support garments are used both during pregnancy and post pregnancy. Most support garments are in the form of underwear or foundation garments. Compression is used for the prevention of deep vein thrombosis and embolism in trauma patients as well as after surgical procedures. Post surgery it has been shown that compression can reduce swelling and provide tissue support which improves the rate and extent of recovery.

Post pregnancy women often have difficulty regaining their pre-pregnancy figure and function. During pregnancy the uterus enlarges to accommodate the developing fetus. The skin over the abdomen along with the abdominal muscles stretch and internal organs displace. After the birth of the baby, the abdomen temporarily remains in an enlarged state and function is impaired. Women often complain that abdominal muscle function never recovers fully and pre pregnancy shape never returns. The surgical procedures (and resultant wounds) required with caesarian deliveries further complicate recovery for women.

During pregnancy, some women suffer from vulval varicosities and pelvic instability. It is known that support garments can help in both reducing the pain and in the treatment of these conditions.

It is the above issues that have brought about the present invention.

SUMMARY OF THE INVENTION

The present invention provides a compression garment comprising panels of elasticised fabric joined by seams of flat lock stitching to define, when worn, specific areas of compression.

Preferably the garment comprises front and rear leg panels, each leg joined at the inside and outside leg; a waist panel joined to the rear leg panels across the bottom; and a crotch panel extending between ends of the front of the waist panel underneath the perineum to join the rear leg panels, whereby the crotch panel is joined to the top of the front leg panels to maximise compression at the perineum.

In another embodiment the waist panel is replaced by a stomach panel, the ends of which are joined at the middle of the back and the under edge is joined across the top of the rear leg panels and across the top of the crotch panel and front leg panels. In one embodiment the compression garment is in the form of shorts that can be worn as outerwear having a conventional waist line. In another embodiment the compression garment comprises shorts that can be worn as an outer garment with an elevated panel that extends underneath the chest providing upper and lower abdominal support. The joins of the panels or seams are strategically placed to avoid common wound areas and the flat lock seam structure eliminates pressure normally caused by bulky seams.

The positioning of the panels and their joining seams is specifically designed to ensure maximum compression in desired areas. In a preferred embodiment various panels of the garment are lined with an open hole mesh fabric that creates a higher level of compression as well as a thin air barrier or space which promotes dryness and a higher level of moisture vapour transfer. In a preferred embodiment a yarn such as nylon is mixed with an elasticised yarn such as elastan, the nylon being approximately 80% of the mixture. The preferred weight is 225 gsm. In a preferred embodiment the panel fabric is a double knit with jersey stitch face. Where a lining fabric is utilised, it too should have a similar percentage of elastic fabric but is produced by a specific stitch pattern to provide a mini open hole mesh.

In one embodiment, the garment is designed:
to be an easily utilized over garment;
to support and compress in all bodily planes which are adversely affected by pregnancy; and
to support abdominal muscles, caesarian and perineal wounds.

In another embodiment, the garment is designed to have similar characteristics to the garment of the previous embodiment. However, in this embodiment the panels are designed to provide increased horizontal compression which, in turn, provides consistent compression to varicosities and increased support to reduce the likelihood of pelvic instability.

DESCRIPTION OF THE DRAWINGS

Embodiments of the present invention will now be described by way of example only with reference to the accompanying drawings in which.

DESCRIPTION OF THE PREFERRED EMBODIMENTS

Figure 1:
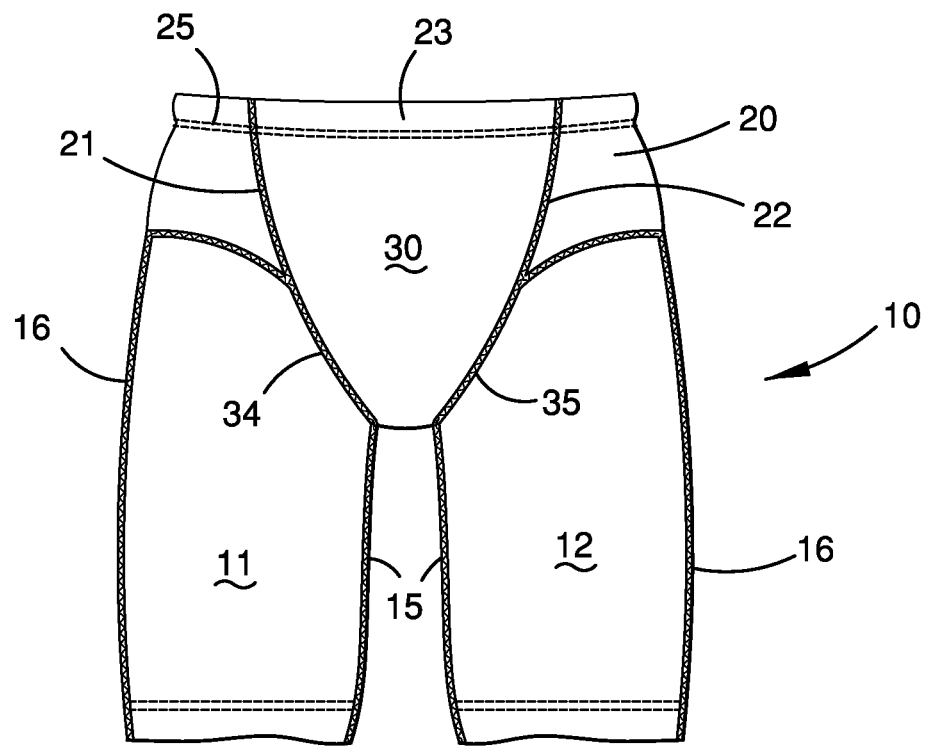
FIG. 1 is a front view of a compression garment illustrating joins between panels of the garment.

In the embodiments shown in FIGS. 1 to 6 two styles of compression garment are illustrated specifically for use as outer garments on women post pregnancy. In the embodiment shown in FIGS. 7 to 9 a compression garment for use as outerwear on women during pregnancy is illustrated.

In the first embodiment shown in FIGS. 1 and 2 a shorter garment 10 is illustrated which sits just below the natural waist line. This garment is more suited to women who have had either caesarian or vaginal delivery. The second embodiment shown in FIGS. 3 and 4 relates to a higher version 50 of the garment with a wide elastic band 70 sitting just under the bra line. This garment 50 is ideally suited to women who are suffering from rectus abdominus stretching. It also provides compression to the perineum and a caesarian wound.

Both garments 10, 50 have been designed so that they can be worn on the first day post caesarian section or as soon as possible after a vaginal delivery. Preferably the garments 10, 50 are designed as outer garments though it is understood that they could serve the role as undergarments.

Both garments 10, 50 are made of elasticised fabric. Strategically cut panels are stitched together using a flat lock seam stitching to reduce high pressure lines and the likelihood of seams aggravating wounds.

Figure 2:
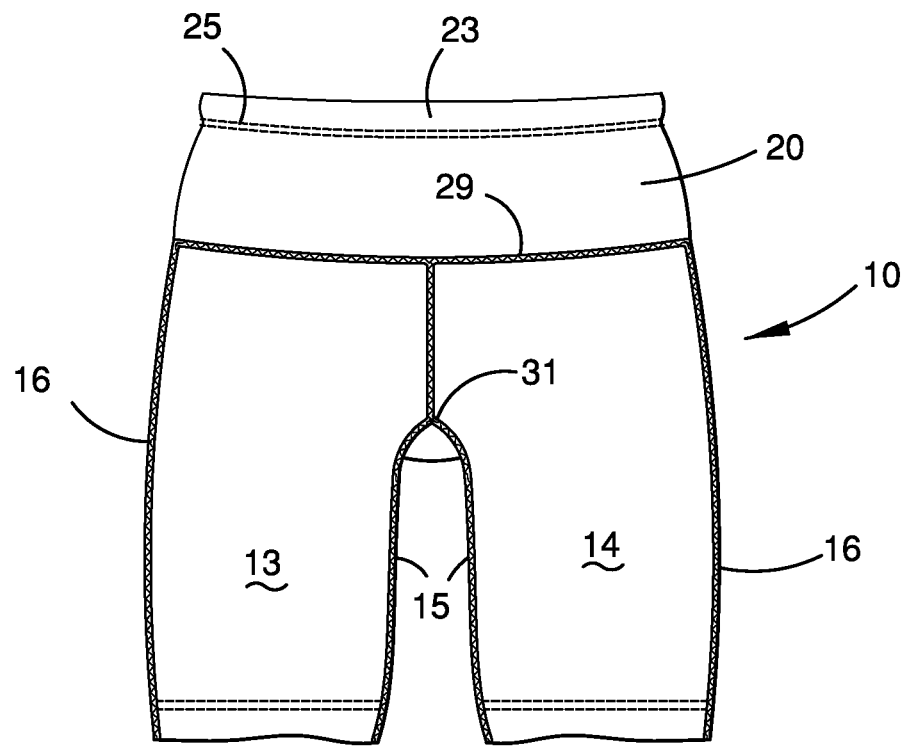
FIG. 2 is a rear view of the garment.

The garment 10 shown in FIGS. 1 and 2 has front 11, 12 and rear 13, 14 leg panels that are joined at the inner 15 and outer 16 sides of both legs. A waist panel 20 extends across the rear of the garment and is joined along a horizontal seam 29 at the top of the wearer's posterior. The waist panel 20 terminates in ends 21, 22 that are joined to a central crotch panel 30. The crotch panel 30 is heart shaped as shown in FIG. 1 and extends under the perineum to join at the base 31 of the posterior at the rear of the garment as shown in FIG. 2. The waist panel 20 includes a 1 inch wide ring of elastic defining a conventional elasticised waist 23. A double needle cover stitched hem 25 finishes the 23 as shown in FIG. 1.

As shown in both FIGS. 1 and 2, the joining of the panels is specifically designed to provide maximum compression to the perineum. Thus, in FIG. 1 the front view, the crotch panel 30 is joined to the top of the front leg panels along seams 34, 35 as well as the ends 21, 22 of the waist panel 20. The joining of the crotch panel 30 to the leg panels 11, 12 is specifically provided to enhance the garment to provide maximum compression in the perineum. The crotch panel 30 and waist panel 20 are lined with an open hole mesh panel (not shown) to maximize compression with better breathability/moisture vapour transfer. The crotch panel 30 and the waist panel 20 are single ply shell fabric with a single ply lining. The leg panels 11-14 are single ply unlined. The end of each leg panel 11-14 is hemmed with a double needle coverstitch.

Figure 3:
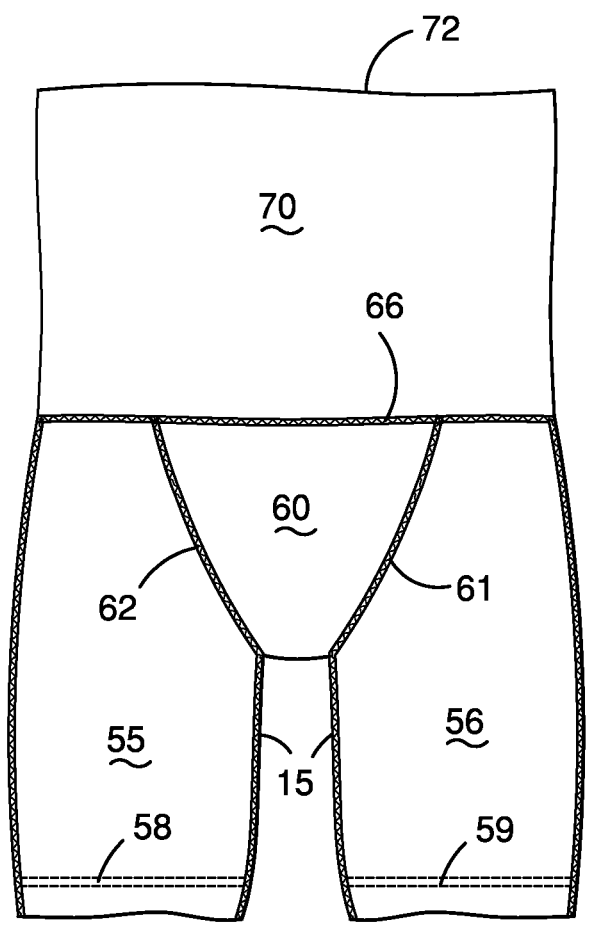
FIG. 3 is a front view of a longer garment.
Figure 4:
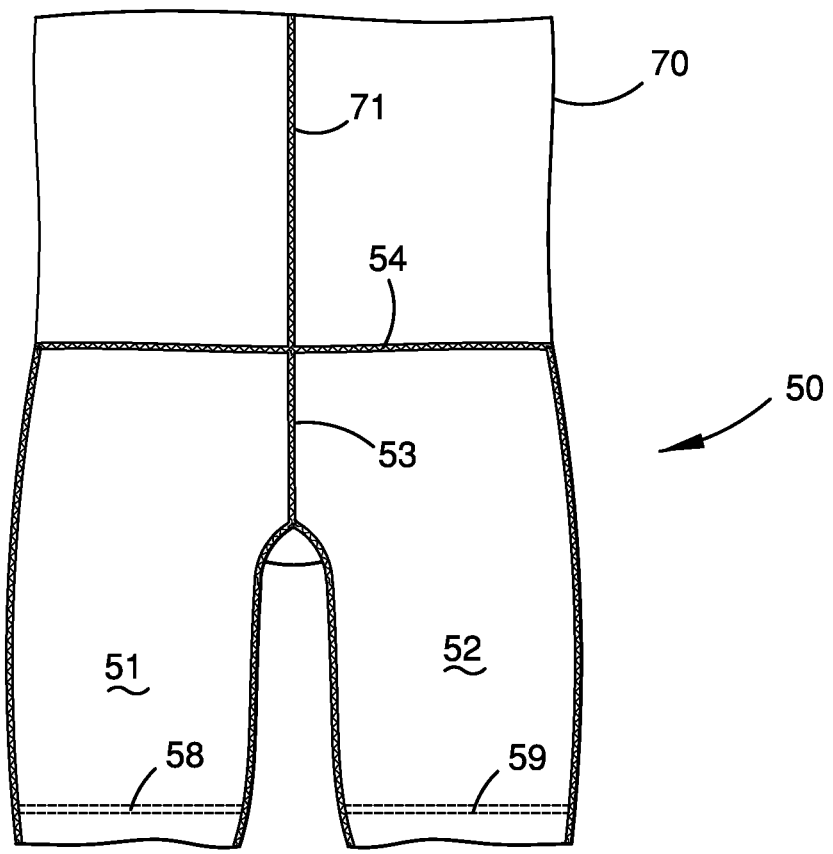
FIG. 4 is a rear view of the longer garment.

In the embodiment shown in FIGS. 3 and 4, a longer garment 50 is provided. In this embodiment the garment comprises rear panels 51, 52 for each leg joined at a vertical seam 53 up the rear of the garment to a horizontal cross seam 54 going across the top of the posterior. The front of the garment 50 shown in FIG. 3 includes a triangular crotch panel 60 that passes under the perineum and is joined through two inclined seams 61, 62 to the inner upper edges of the front leg panels 55, 56. A horizontal seam 66 runs across the top of the leg panels 55, 56 and crotch panel 60 at the same height as the seam 54 at the rear. A stomach panel 70 comprises a band of fabric that has been doubled and is joined at the rear as shown in FIG. 4 by a vertical seam 71. The band 70 extends from the waist to a position just below the chest line. A band of a strip of elastic 72 is encased in the top of the panel 70 to help anchor the panel. The crotch panel 60 is lined with an open hole power mesh to maximise compression for better breathability/moisture and vapour transfer. Double needle coverstitched hems 58, 59 can be placed at the lower ends of each leg portion.

Figure 5A:
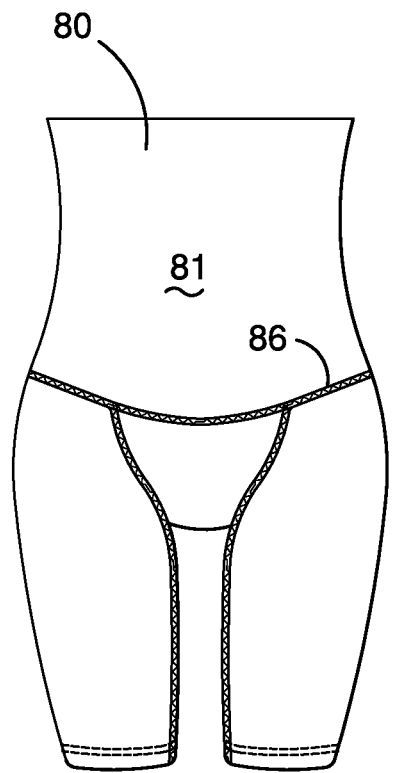
FIG. 5a is a front view of a modified form of the longer garment shown in FIGS. 3 and 4.
Figure 5B:
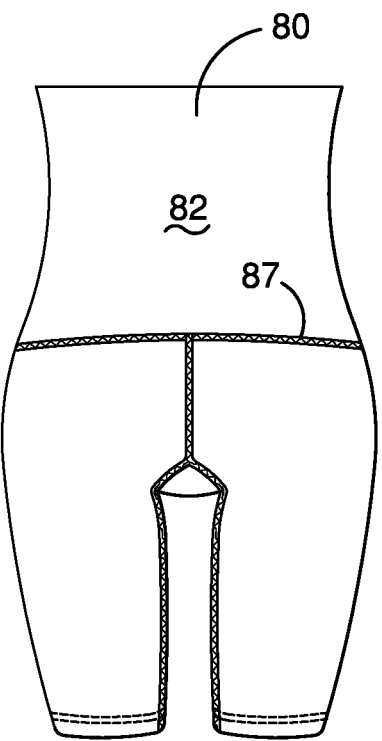
FIG. 5b is a rear view of the garment.
Figure 6A:
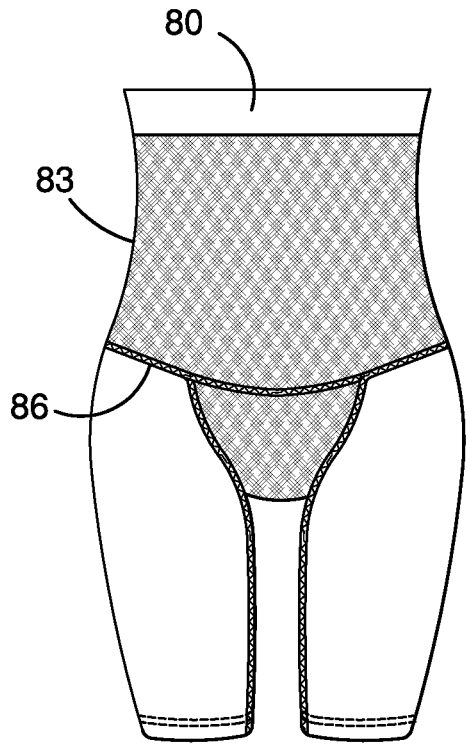
FIGS. 6a and b are inside front and rear views of the garment.
Figure 6B:
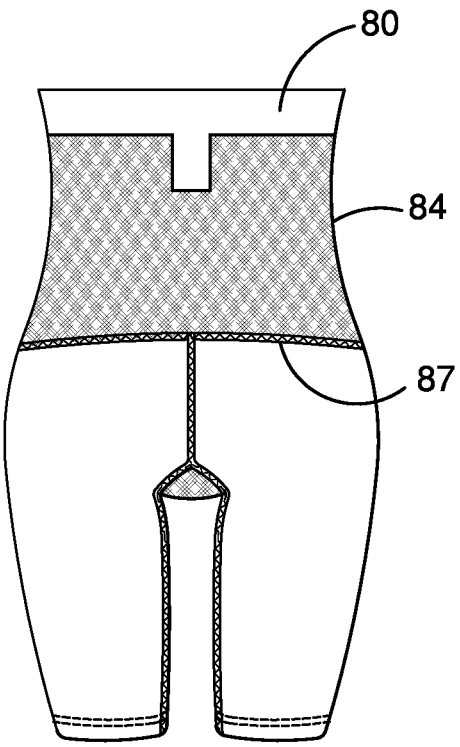

In a third embodiment shown in FIGS. 5 and 6, a more profiled longer garment is provided in which the stomach panel 80 comprises a contoured outer front panel 81 and contoured back panel 82 joined by side seams. The crotch panels are similar to crotch panel 30. The front and back panels 81, 82 are lined by open hole mesh lining panels 83, 84 which are also contoured. Shaped flat-locked side seams provide better contour and more effective compression of the waist and upper abdomen. The horizontal waist and rear posterior seams 86, 87 are also contoured for more effective compression at the lower abdomen.

Figure 7:
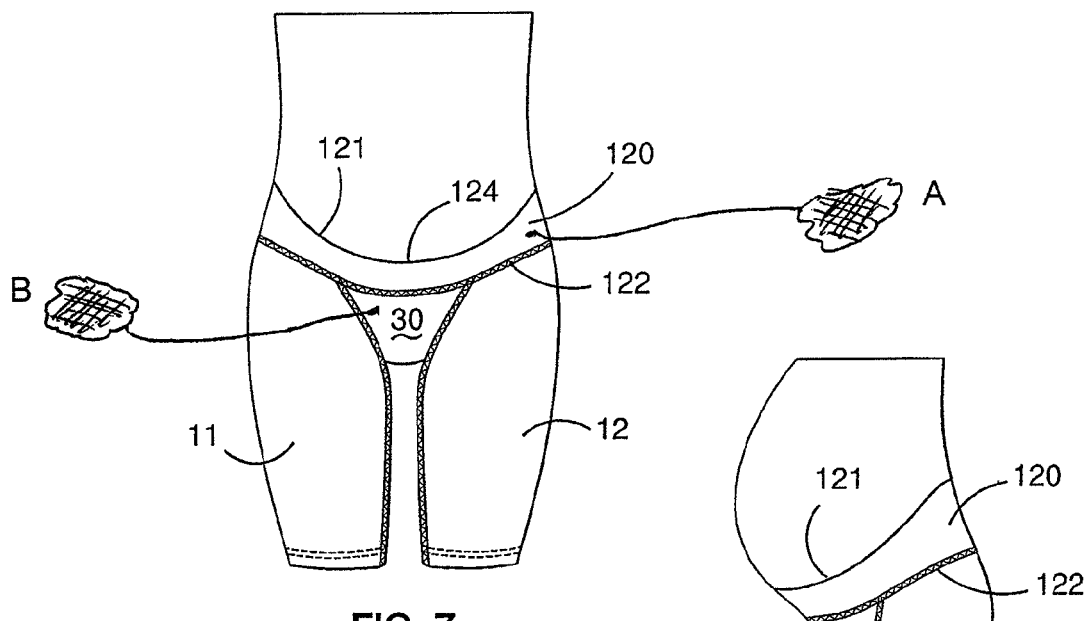
FIG. 7 is a front view of a pregnancy garment.
Figure 8:
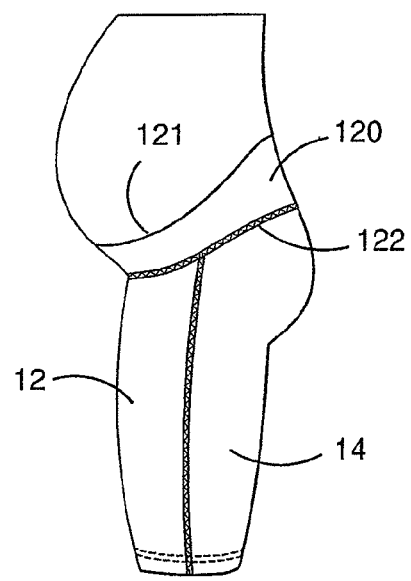
FIG. 8 is a side view of the pregnancy garment.
Figure 9:
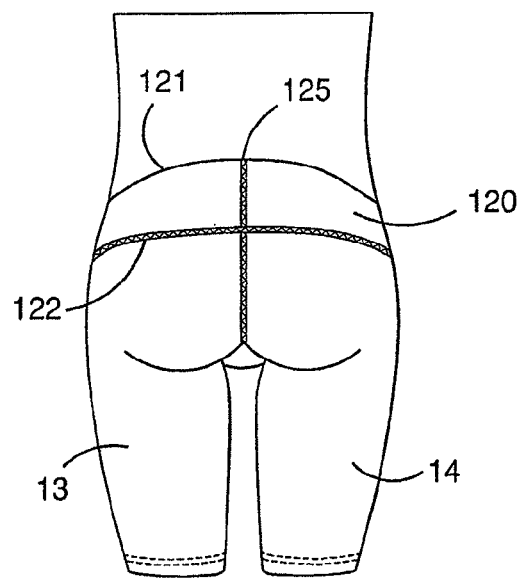
FIG. 9 is a back view of the pregnancy garment.

In a fourth embodiment shown in FIGS. 7, 8 and 9, a compression garment is illustrated specifically for use during pregnancy. During the end of the pregnancy term, some women suffer from vulval varicosities which are effectively varicose veins of the vulva. During pregnancy, the valves in the veins do not work as well due to pregnancy hormones which can result in blood pooling in the veins making existing varicose veins worse. Vulval varicosities cause irritation or aching discomfort. Support garments help reduce the irritation and pain.

Pelvic instability is a condition which causes pain around the joins of the pelvis during pregnancy. The hormones associated with pregnancy can cause the joints of the pelvis to loosen which can result in the pelvis becoming unstable or out of alignment. Furthermore, pregnancy places strain on the muscles of the back, stomach, pelvic floor, hips and pelvic girdle which may lead to the pelvic joints becoming less stable. It is thought that support garments help to reduce the effects and pain associated with pelvic instability.

The garment shown in FIGS. 7 to 9 is specifically constructed to create panels for maximum support of the back and the pelvis and to provide compression of the vulva and labia. This support helps manage pelvic instability and reduce the pain from varicosities. The garment is very similar to the garment shown in FIGS. 1 and 2 with identical front and rear leg panels 11, 12, 13, 14 and a similar crotch panel 30 but with a modified waist panel 120. In this embodiment, the waist panel 120 is in the form of an ergonomically shaped belt that extends around the torso to maintain consistent contact with the back and sides to create maximum compression for the vulval and labial areas. The belt comprises two outer fabric layers plus an internal lining layer of open hole mesh for additional support and breathability. The waist belt 120 has upper and lower edged 121, 122. The top edge 121 includes a half inch strip of elastic included in the top edge seam for stability.

The waist belt 120 is narrow as it sits above the symphysis pubis (pubic bone) and then widens outwardly with its maximum width at the lumbar-sacral area at the rear. In a preferred embodiment, the waist band is about 2½ inches at the narrowest point 124 and increases outwardly to approximately 4½ inches at the centre of the back 125. The V-shaped crotch panel 30 extends from the front to the rear for horizontal compression of varicosities. The horizontal compression takes place in conjunction with the stabilized belt 120 and leg panels 11-14. The crotch panel 30 and belt 120 are constituted by two outer layers and an internal open hole mesh lining layer, as shown diagrammatically at B in FIG. 7. The leg panels 11-14, which finish above the knee, help to maintain placement of the crotch panel 30 to provide consistent compression to varicosities. Each leg panel is a single layer of outer fabric.

FIGS. 7, 8 and 9 are front, side and rear views and show the contouring and positioning of the waist band across the front, sides and rear of a pregnant torso.

The crotch panels, which overlie the perineum, are also referred to as perineum panels. The waist and stomach panels to which the crotch/perineum panel is joined in the front are also referred to as body panels.

The fabric used in the outer layers of the garments described above is elasticised and preferably comprises 75-85% nylon yarn with 25-15% elastan. The preferred weight is 225 gsm. The yarn is preferably nylon and the elasticised material is spandex.

In a preferred embodiment the most appropriate knit stitch to achieve the desired stretch and recovery is to be a jersey stitch face in a double knit construction. However it is also understood that other knitting stitches are envisaged as being suitable.

Recovery should be immediate with no more than +3% variation from the relaxed pre-stretched state to relaxed state immediately after stretch and recovery. The +3% should decrease to 0% variance within 30 minutes. The lining fabric should have a similar content of elastan in an open hole mesh knit stitch pattern. The weight of the lining should be 170 gsm.

Whilst these garments have been specifically designed to be worn by women during pregnancy and post delivery, it is understood that these garments may also be used by both male and female patients post surgery. Abdominal surgery such as hernias, appendicitis, liposuction and other plastic surgery provide opportunities for post operative treatment using compressing garments of the kind described above.

The garments provide compression to specific areas and have been designed so that maximum compression is positioned where most needed. It is known that continuous compression on a wound or a swollen area aids recovery by decreasing swelling, improving blood supply thus draining the products of inflammation more effectively. This accelerates the healing process and provides an opportunity for a woman to return to a pre-pregnancy shape more quickly.

Other benefits include reduction and tension of abdominal muscles along with reduced tension over a surgical wound site. The garments provide the patient with core support along with greater ability to return to a daily routine after delivery or surgery. The compression provided by the garment reduces abdominal and perineum tension whilst lifting, bathing and caring for a new born baby.

The sizes of the garments would vary to cover wearers of all sizes.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:

1. A compression garment to be worn during or after pregnancy, comprising:
   a pair of legs comprising left front and rear leg panels, and right front and rear leg panels, the rear leg panels joining together at a central seam,
   a body panel attached to a top portion of the pair of legs such that the body panel in use will at least partially encircle a wearer's body, and
   a crotch panel disposed between the pair of legs and attached to the body panel at a front of the compression garment, the crotch panel being attached at front lateral seams to the two front leg panels and extending to the two rear leg panels to which the crotch panel attaches at two rear seams that converge upon the central seam so that, the frontal lateral seams and rear seams are positioned, in use, to be clear of a wearer's perineum, and
   wherein the panels of the garment are formed from an elasticized fabric, the crotch panel being formed of at least 2 ply of elasticized fabric, and the frontal lateral seams, rear seams, and the central seam are flat-lock seams to minimize line pressure at the seams of the garment to, in use, exert consistent compression across the crotch panel onto the wearer's perineum.

2. The compression garment according to claim 1, the body panel being a waist panel joined to the rear leg panels by a horizontal seam across the bottom of the waist panel; and the crotch panel extending downwardly from the waist panel and continuing, in use, underneath the perineum of the wearer to join the rear leg panels at the two rear converging seams to maximize compression across the crotch panel, in use, onto the wearer's perineum.

3. The compression garment according to claim 1 wherein the body panel is a waist panel which is a belt joined by a flat-lock seam at the back, said seam forming an extension of the central seam, and being joined to the tops of both of the front and rear leg panels and in front, to the top of the crotch panel.

4. The compression garment according to claim 1, wherein the belt comprises two outer fabric layers over an internal lining layer of open hole mesh, and the crotch panel comprises two outer layers having an internal open mesh lining layer.

5. The compression garment according to claim 1 wherein the front and rear leg panels comprise a single layer of elasticized fabric.

6. The compression garment according to claim 1, wherein the body panel is a stomach panel joined to the rear leg panels by a horizontal seam across the bottom of the stomach panel; and the crotch panel extending from the stomach panel and continuing, in use, underneath the perineum of the wearer to join the rear leg panels at the two rear converging seams, the crotch panel being joined by the frontal lateral seams to the tops of the front leg panels and to the front stomach panel to maximize compression across the crotch panel onto the wearer's perineum.

7. The compression garment according to claim 6 wherein the stomach panel and the crotch panel comprise a layer of knitted elasticized fabric backed by a liner of open mesh elasticized fabric.

8. The compression garment according to claim 1 wherein the elasticized fabric comprises a mixture of nylon and elastan.

9. The compression garment according to claim 8 wherein the mixture is 75-85% nylon and 15-25% elastan.

10. The compression garment according to claim 1 wherein the elasticized fabric comprises a double knit fabric having a jersey stitch face.

11. The compression garment according to claim 1 wherein at least one panel is lined by a liner of open mesh, elasticized fabric.

12. The compression garment according to claim 1, wherein the body panel is a stomach panel which, in use, covers and compresses a caesarian wound area and the rectus abdominus muscles of the wearer.

13. The compression garment according to claim 1, wherein the body panel provides compression, in use, to the pelvic joints.

14. A compression garment to be worn during or post pregnancy, comprising:
   a pair of legs;
   a body panel attached to a top portion of the pair of legs such that the body panel in use will at least partially encircle a wearer's body; and
   a crotch panel disposed between the pair of legs and joined by flat-lock seams to the pair of legs, the crotch panel attached to the body panel at a front of the compression garment and the flat-lock seams converging together at a rear of the garment, said flat-lock seams minimizing line pressure at the seams of the garment,
   wherein the panels of the garment are formed from an elasticized fabric, the crotch panel being formed of at least two ply of elasticized fabric, and wherein the seams adjoining the panels are positioned, in use, to be clear of a wearer's perineum, and the panels are configured to, in use, apply consistent compression across the crotch panel onto the wearer's perineum.

15. The compression garment according to claim 14, wherein the crotch panel comprises at least one outer layer of elasticized fabric and an internal liner layer of open mesh.

16. The compression garment according to claim 14, wherein the crotch panel is formed of at least three ply of elasticized fabric.

17. The compression garment according to claim 14, wherein the pair of legs comprise a single layer of elasticized fabric.

18. The compression garment according to claim 14, wherein the body panel is a stomach panel which, in use, covers and compresses a caesarean wound area and the rectus abdominus muscles of the wearer.

19. The compression garment according to claim 14, wherein the body panel is a stomach panel, the stomach panel being arranged to extend towards a chest line.

20. The compression garment according to claim 14, wherein the body panel comprises at least two ply of elasticized fabric.

\* \* \* \* \*

UNITED STATES PATENT AND TRADEMARK OFFICE
CERTIFICATE OF CORRECTION

| | |
|---|---|
| PATENT NO. | : 8,784,351 B2 |
| APPLICATION NO. | : 12/405331 |
| DATED | : July 22, 2014 |
| INVENTOR(S) | : Dumpson et al. |

It is certified that error appears in the above-identified patent and that said Letters Patent is hereby corrected as shown below:

On the title page, item (73) Assignee, please change "Gilheany & O'Donovan Holdings Pty," to -- Gilheany & O'Donovan Holdings Pty Ltd. --.

Signed and Sealed this
Fourteenth Day of June, 2016

Michelle K. Lee
*Director of the United States Patent and Trademark Office*